United States Patent [19]
Talish et al.

[11] Patent Number: 5,556,372
[45] Date of Patent: Sep. 17, 1996

[54] APPARATUS FOR ULTRASONIC BONE TREATMENT

[75] Inventors: Roger J. Talish, Fairfield; John P. Ryaby, Essex Fells; Kenneth J. Scowen, Springfield; Kenneth J. Urgovitch, Clifton, all of N.J.

[73] Assignee: Exogen, Inc., West Caldwell, N.J.

[21] Appl. No.: 389,148

[22] Filed: Feb. 15, 1995

[51] Int. Cl.⁶ .................................................. A61B 17/56
[52] U.S. Cl. .................................. 601/2; 607/7; 607/50; 607/51; 602/2; 128/660.03
[58] Field of Search .................... 128/660.03, 660.01, 128/661.07, 662.03, 662.04; 600/15; 601/2; 602/2; 607/7, 50, 51, 97, 151, 152

[56] References Cited

U.S. PATENT DOCUMENTS

| | | | |
|---|---|---|---|
| 2,799,787 | 7/1957 | Güttner et al. | |
| 3,499,437 | 3/1970 | Balamuth | 128/24 |
| 4,175,565 | 11/1979 | Chiarenza et al. | 433/32 |
| 4,530,360 | 7/1985 | Duarte | 128/419 F |
| 4,708,127 | 11/1987 | Abdelghani | 128/24 A |
| 5,003,965 | 4/1991 | Talish et al. | 128/244 AA |
| 5,186,162 | 2/1993 | Talish et al. | 128/24 AA |
| 5,211,160 | 5/1993 | Talish et al. | 128/24 AA |
| 5,259,384 | 11/1993 | Kaufman et al. | 128/660.01 |
| 5,309,898 | 5/1994 | Kaufman et al. | 601/2 |
| 5,314,401 | 5/1994 | Tepper | 600/14 |
| 5,415,167 | 5/1995 | Wilk | 128/653.1 |

FOREIGN PATENT DOCUMENTS

| | | |
|---|---|---|
| 47359 | 3/1987 | Japan. |
| 47358 | 3/1987 | Japan. |
| 82569 | 3/1992 | Japan. |
| 82568 | 3/1992 | Japan. |
| 82567 | 3/1992 | Japan. |
| 269159 | 10/1993 | Japan. |

OTHER PUBLICATIONS

T. Arai et al., "The Effect of Ultrasound Stimulation On Disuse Osteoporosis", Thirteenth Annual Meeting of BRAGS Dana Point, CA, 1993.

Primary Examiner—Krista M. Zele
Assistant Examiner—Shawna J. Shaw
Attorney, Agent, or Firm—Dilworth & Barrese

[57] ABSTRACT

The apparatus is used for therapeutically treating injuries using ultrasound. The apparatus includes an ergonomically constructed ultrasonic transducer treatment head module partially fabricated with a conductive plastic material. The apparatus also utilizes a portable, ergonomically constructed main operating unit constructed to fit within a pouch worn by the patient. In operation, the transducer treatment head module is positioned adjacent the area of the injury and excited for a predetermined period of time. To ensure that the transducer treatment head module is properly positioned, and to insure compliance with a treatment protocol, a safety interlock is provided to prevent inadvertent excitation of the transducer.

16 Claims, 11 Drawing Sheets

5,556,372

APPARATUS FOR ULTRASONIC BONE TREATMENT

BACKGROUND OF THE INVENTION

1. Field of the Invention

The present invention relates to an apparatus for therapeutically treating injuries using ultrasound. More particularly, the present invention relates to an apparatus which utilizes a portable ergonomically constructed signal generator and an ergonomically constructed transducer for treating bone injuries or a variety of musculoskeletal injuries and/or problems.

2. Description of the Related Art

The use of ultrasound to therapeutically treat and evaluate bone injuries is known. Impinging ultrasonic pulses having appropriate parameters, e.g., frequency, pulse repetition, and amplitude, for suitable periods of time and at a proper external location adjacent to a bone injury has been determined to accelerate the natural healing of, for example, bone breaks and fractures. For patients with reduced healing capacity, such as elderly persons with osteoporosis, ultrasonic therapy may promote healing of bone injuries that would otherwise require prosthetic replacement or leave the patient permanently disabled.

U.S. Pat. No. 4,530,360 to Duarte describes a basic non-invasive therapeutic technique and apparatus for applying ultrasonic pulses from an operative surface placed on the skin at a location adjacent a bone injury. The applicator described in the '360 patent has a plastic tube which serves as a grip for the operator, an RF plug attached to the plastic tube for connection to an RF source, and internal cabling connected to an ultrasonic transducer. To apply the ultrasound pulses during treatment an operator must manually hold the applicator in place until the treatment is complete. As a result, the patient is, in effect, immobilized during treatment. The longer the treatment period, the more the patient is inconvenienced. The '360 patent also describes a range of RF signals for creating the ultrasound, ultrasound power density levels, a range of duration for each ultrasonic pulse, and a range of ultrasonic pulse frequencies.

U.S. Pat. No. 5,003,965 to Talish et al. relates to an ultrasonic body treatment system having a body-applicator unit connected to a remote control unit by sheathed fiber optic lines. The signals controlling the duration of ultrasonic pulses and the pulse repetition frequency are generated apart from the body-applicator unit. Talish et al. also describes a mounting fixture for attaching the body-applicator unit to a patient so that the operative surface is adjacent the skin location.

While the systems described in these patents relate to therapeutic methods and apparatus for ultrasonically treating injured bone, they do not disclose ergonomically configured signal generators and transducers which permit patient mobility during treatment. Moreover, such systems do not describe techniques for positioning the transducer at the approximate external skin location of the injury to optimize the ultrasonic therapy received.

Therefore, a need exists for apparatus which optimize healing while maintaining patient mobility. Also a need exists for an apparatus for determining an external location on the patient's body corresponding to the location of an internal bone injury.

SUMMARY OF THE INVENTION

The ultrasonic treatment apparatus of the present invention is used for therapeutically treating injuries using ultrasound. The apparatus includes an ergonomically constructed Ultrasonic transducer treatment head module with an integral signal generator which provides excitation signals for an ultrasonic transducer within the module. The portable main operating unit is constructed to fit within a pouch worn by the patient and provides treatment timing control circuitry as well as monitoring circuitry for the proper attachment and operation of the transducer assembly. In operation, the module is positioned adjacent the area of the injury and excited for a predetermined period of time. To ensure that the transducer treatment head module is properly positioned, a safety interlock is provided to insure compliance with the treatment protocol and to prevent inadvertent excitation of the transducer assembly.

Preferably, the main operating unit has an internal power source for powering the signal generator circuitry in the transducer treatment head module, a display coupled to said signal generator circuitry to display treatment sequence data, a keypad coupled to said signal generator circuitry to permit user operation and/or entry of data, said signal generator circuitry including a processor, means for generating a pulsed control signal, and a switch coupled to said processor for regulating said pulsed control signal. A communication interface may be connected between a communication port and the processor to provide a communication link between the ultrasonic signal generator and an external computer or modem. Preferably, the communication interface is a serial communication interface, however, a parallel interface is also contemplated. An alarm is provided to indicate to the user that the treatment time has expired. The alarm is coupled to the processor such that when ultrasonic treatment is completed the processor activates the alarm and terminates ultrasound generation.

To ensure that the transducer treatment head module is properly positioned prior to exciting the ultrasonic transducer, a safety interlock mechanism is provided. The transducer treatment head module is configured to inter fit with a fixture positioned adjacent the injury. The fixture has an aperture configured to receive a portion of the ultrasonic transducer treatment head module. At least two bayonet lugs connected to the fixture and extending into the aperture, are electrically connected to form a conductive path therebetween. In addition, the ultrasonic transducer treatment head module includes at least two slotted lugs having at least a portion thereof extending from an outer surface of the module. The slotted lugs are configured to engage at least two bayonet lugs and are fabricated from conductive plastic such that when the slotted lugs engage the bayonet lugs a conductive path is formed between the slotted lugs. In this configuration, the processor sends a safety interlock signal to the transducer treatment head module along one conductor and the conductive path between slotted lugs returns the safety interlock signal to the processor along another conductor. When the processor receives the return safety interlock signal, the transducer can now be excited. This feature insures that the patient correctly complies with the ultrasound protocol and that the actual treatment is accurately recorded.

The present invention also provides a kit for ultrasonically treating injuries while maintaining patient mobility. The kit includes an ultrasonic transducer treatment head module, a fixture configured to be worn by a patient adjacent the injury and configured to receive at least a portion of the ultrasonic transducer treatment head module, an integrated ultrasonic signal generator located in the ultrasonic transducer treatment head module, a main operating unit (MOU) or controller and a pouch constructed to receive the MOU. Preferably, the pouch has a belt and a shoulder strap which can be releasably secured to a patient during treatment thereby providing patient mobility.

It is a further feature of the present invention that a single or a plurality of transducer treatment head modules can be attached to a single MOU and be selectively controlled thereby.

A method for ultrasonically treating musculoskeletal injuries and surface injuries such as, for example, open wounds, burns and venous ulcers, while maintaining patient mobility is also provided. Initially, the location of the injury is determined. Once the location of the injury is ascertained, a fixture is affixed to the patient adjacent the location. Preferably, the fixture is configured to receive at least a portion of an ultrasonic transducer assembly which is releasably secured to the fixture. A pouch having the MOU therein is releasably secured to the patient and is connected to the transducer treatment head module. The signal generator in the transducer housing is then activated so as to excite an ultrasonic transducer to impinge ultrasonic waves against the injury. To permit patient mobility during treatment, the MOU has an internal power source.

BRIEF DESCRIPTION OF THE DRAWINGS

Preferred embodiments of the invention are described below with reference to the drawings, which are described as follows.

DETAILED DESCRIPTION OF THE PREFERRED EMBODIMENTS

The ultrasonic treatment apparatus of the present invention is used for therapeutically treating injuries using ultrasound. Although shown here for the treatment of musculoskeletal injuries, other injuries including venous ulcers are also contemplated. The apparatus includes an ergonomically constructed ultrasonic transducer assembly partially fabricated with a conductive plastic material. The apparatus also utilizes a portable, ergonomically constructed main operating unit (MOU) which provides control signals for the ultrasonic transducer treatment head module. The portable MOU is constructed to fit within a pouch worn by the patient. In operation, the transducer treatment head module is positioned adjacent the injured area and excited for a predetermined period of time. To ensure that the transducer treatment head module is properly positioned, a safety interlock is provided to prevent inadvertent excitation of the transducer assembly and to insure patient compliance.

Figure 1:
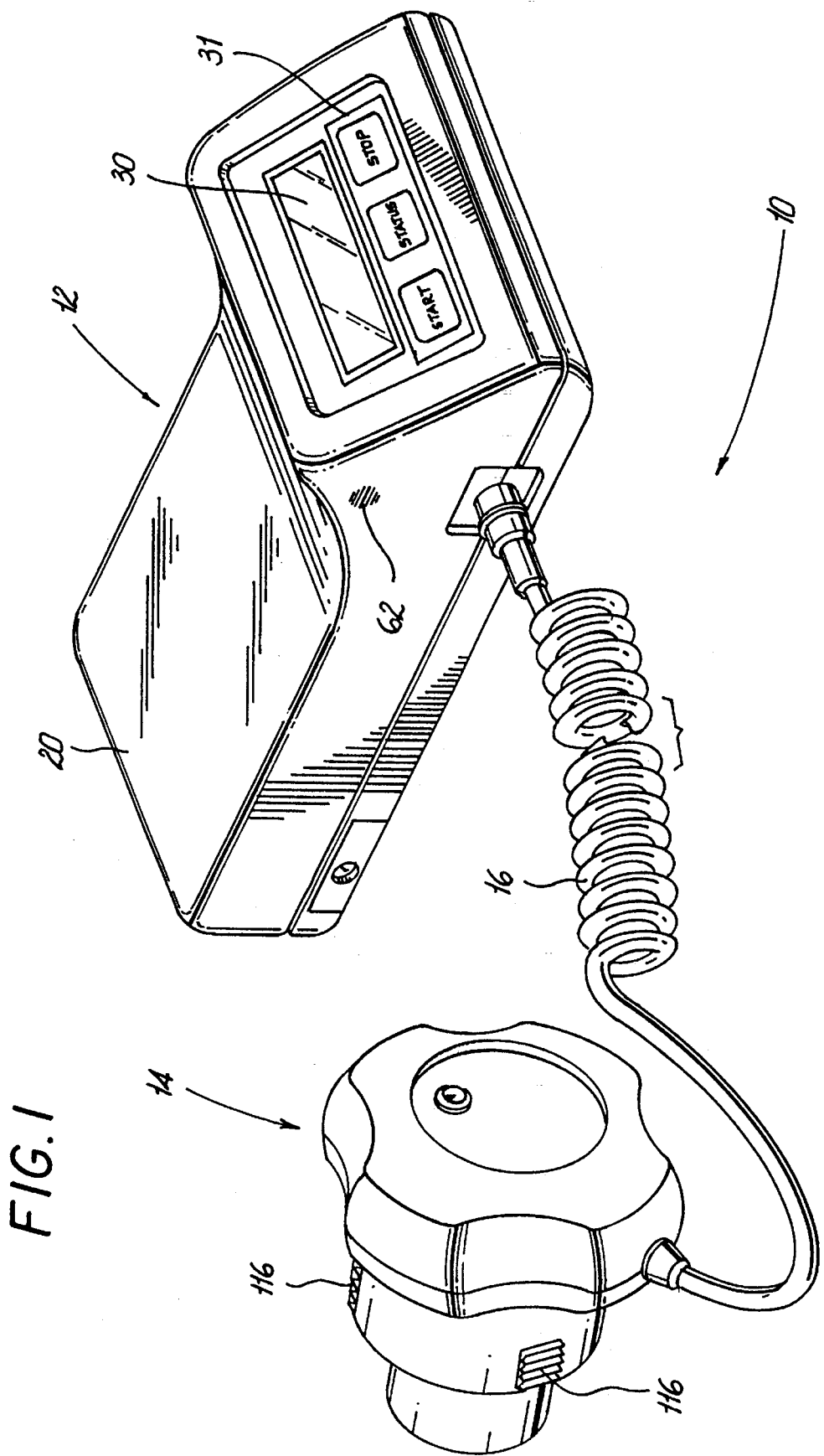
FIG. 1 is a perspective view of a portable ultrasonic treatment apparatus according to the present invention, illustrating a main operating unit or controller and an ultrasonic transducer treatment head module.
Figure 2:
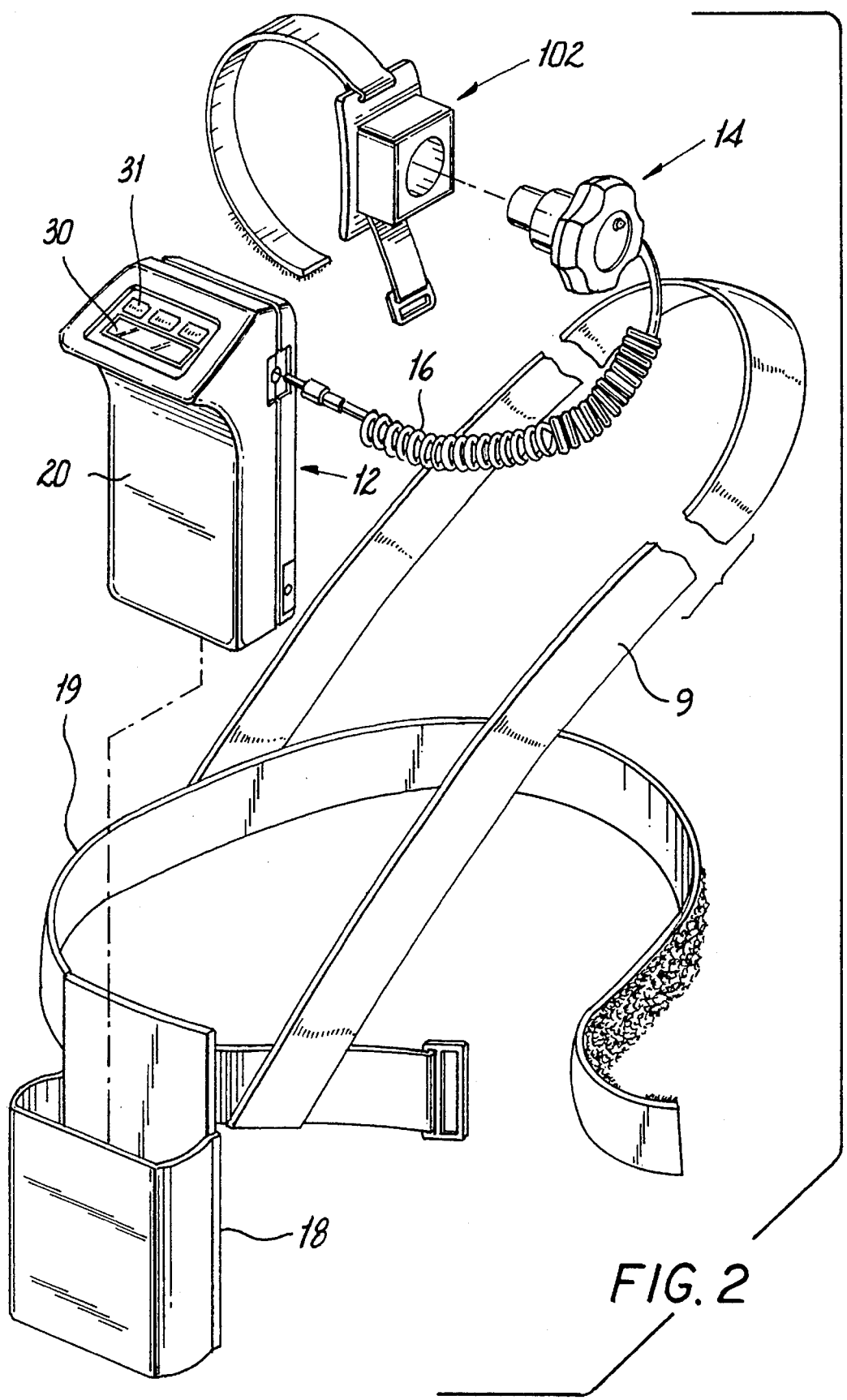
FIG. 2 is a perspective view with parts separated of the main operating unit and transducer head module of FIG. 1 and a pouch shoulder strap and belt for patient mobility during treatment.
Figure 3:
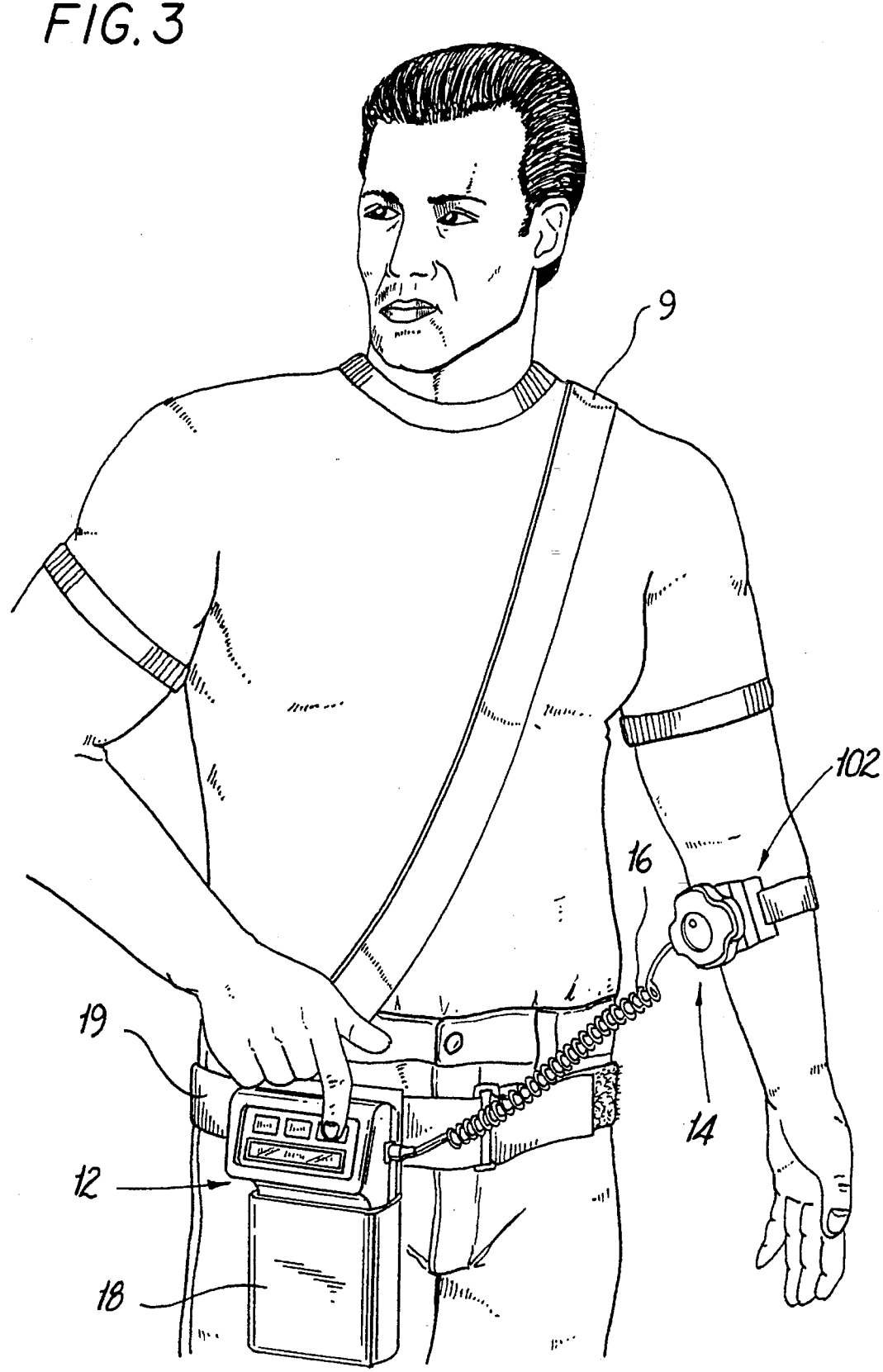
FIG. 3 is a perspective view of a patient wearing the portable treatment apparatus according to the present invention during treatment.

Turning to the figures, in particular FIG. 1, the portable ultrasonic treatment apparatus 10 of the present invention is shown. The ultrasonic treatment apparatus 10 includes an MOU 12 and an ultrasonic transducer treatment head module 14 coupled to the MOU 12 by cable 16. The MOU 12 is ergonomically configured and constructed to fit with a pouch 18 which is worn by the patient using belt 19 and shoulder strap 9, as shown in FIGS. 2 and 3. Cable 16 is preferably a multi-conductor cable capable of transmitting relatively low frequency or optical signals, as well as digital signals. Cable 16 may include coaxial cable or other type of suitable shielded cable. Alternatively, cable 16 may include fiber optic cable for transmitting optical signals.

Figure 4:
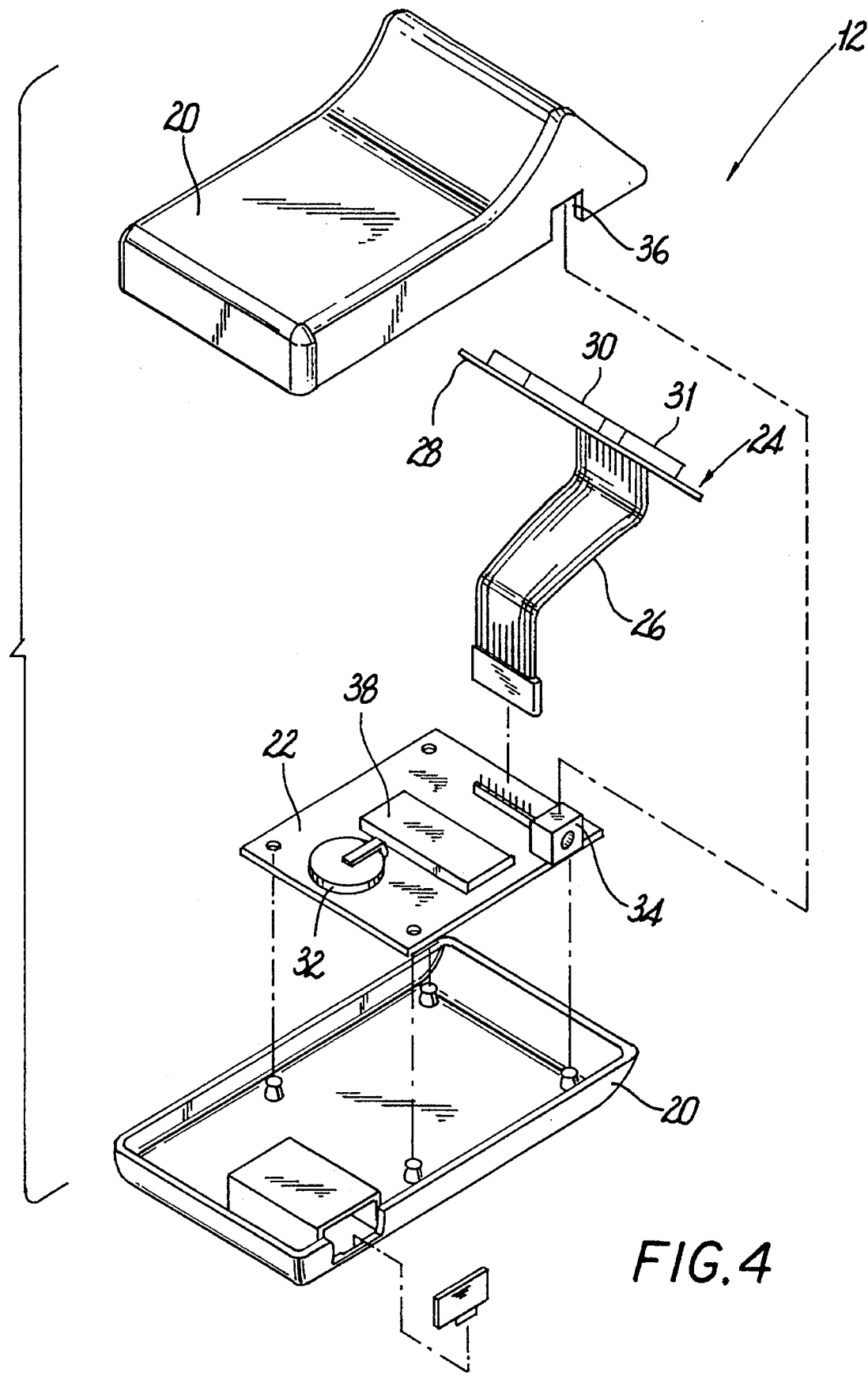
FIG. 4 is an exploded view of the main operating unit of FIG. 1.

Referring to FIG. 4, MOU 12 includes a housing 20 which is typically constructed in two half-sections joined together by screws, ultrasonic welds or adhesives. A printed circuit board 22 is positioned within the housing 20 and coupled to display assembly 24 via cable 26. Display assembly 24 includes mounting board 28, display 30 and a keypad 31, shown in FIG. 1. Display 30 may be, for example, a liquid crystal type display or an LED type display suitable for displaying text and numerals. Battery holder 32 is connected to printed circuit board 22 for portable operation of the real time clock and the ultrasonic treatment head module of the present invention. In addition, a suitable battery, such as a bank of three (3) lithium batteries is positioned in the battery compartment.

Communication port 34 is affixed to printed circuit board 22 and accessible through channel 36 in housing 20. Communication port 34 is coupled to signal generator circuitry 38 on printed circuit board 22 and provides a communication link, e.g., for serial communications, between the signal generator 12 and an external computer. In this configuration, a physician can download information, such as the number, date, time of day, and/or duration of actual treatments initiated by the patient, stored within signal generator circuitry 38.

Figure 5:
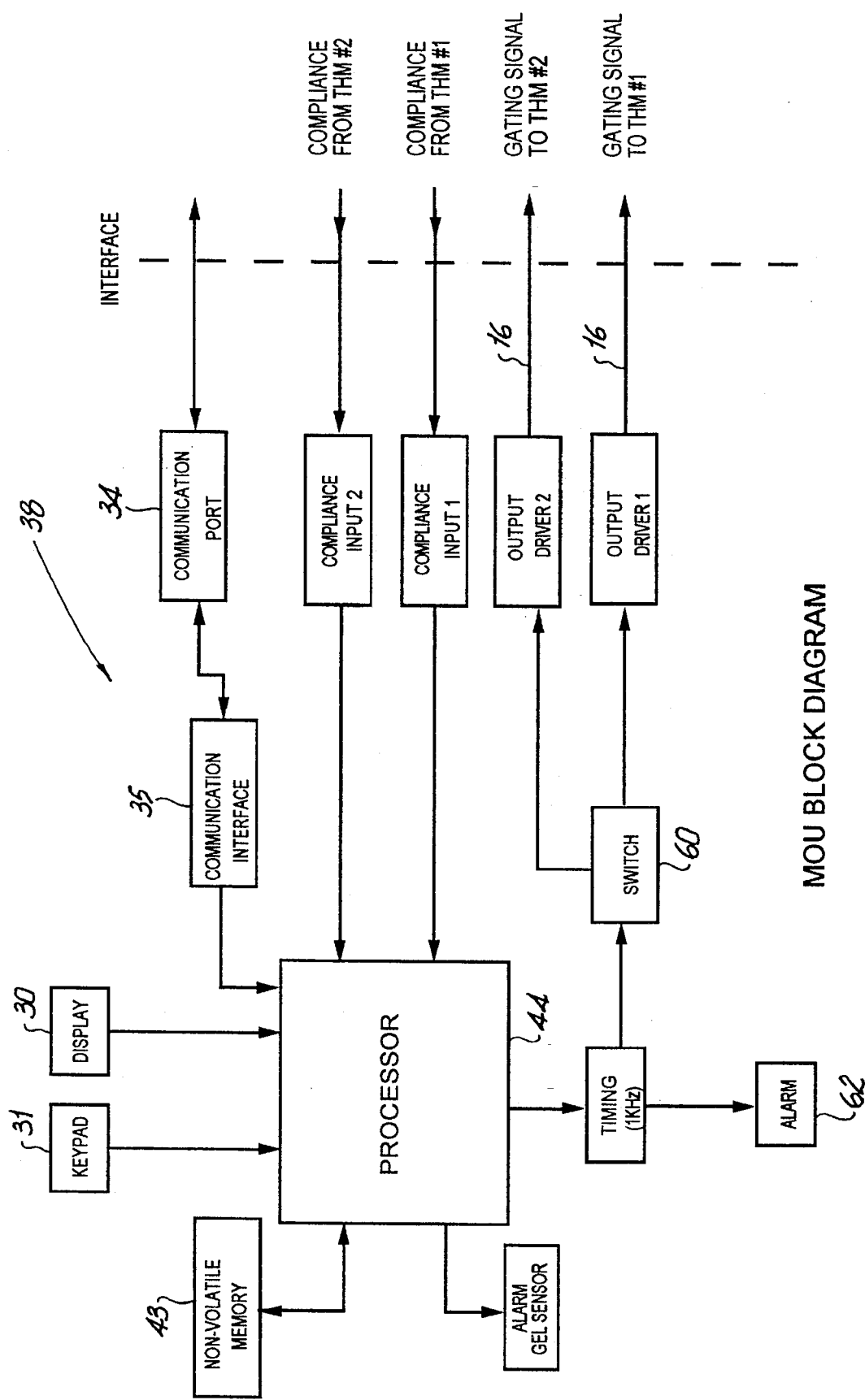
FIG. 5 is a block diagram of the circuitry for the main operating unit of FIG. 1.

FIG. 5 illustrates a block diagram of the signal generator circuitry 38 within the signal generator 12 which generates and controls the pulses transferred to the ultrasonic transducer assembly 14. Preferably, signal generator circuitry 38 includes a processor 44 having memory 43 (e.g., RAM and ROM) and stored programs (e.g., system and application) for controlling the operation of the processor, as well as the transducer treatment head module 14. Processor 44 is coupled to display 30 and keypad 31 and is configured to receive data from the keypad 31 and to transfer data to the display 30. Processor 44 may include a microprocessor, such as the Intel® 80/x86 family of microprocessors, or processor 44 may be a microcontroller having internal memory. Communication interface 35 is connected between communication port 34 and processor 44 and is provided to communicate with, for example, an external computer. Communication interface 35 may be a serial interface, such as an RS-232 interface, a parallel interface, or a modem.

Processor 44 is also utilized to control the treatment sequence, i.e., the start time and the stop time of the ultrasonic treatment. The processor may be preprogrammed for treatment times and the user (e.g. the physician or patient) selects one of the treatment times via keypad 31, or the processor may be programmed by the user via keypad 31 to set the start and stop sequence. Typical treatment times may range between 1 and 55 minutes, although treatments in the order of 10–20 minutes are typical. When the treatment time is activated, processor 44 closes switch 60 which permits the modulated signal to pass to cable 16. When the treatment time expires, switch 60 is opened and the modulated signal is inhibited from passing to cable 16. In addition, when the treatment time expires, processor 44 may send an alarm signal to alarm 62 which activates.

Figure 6:
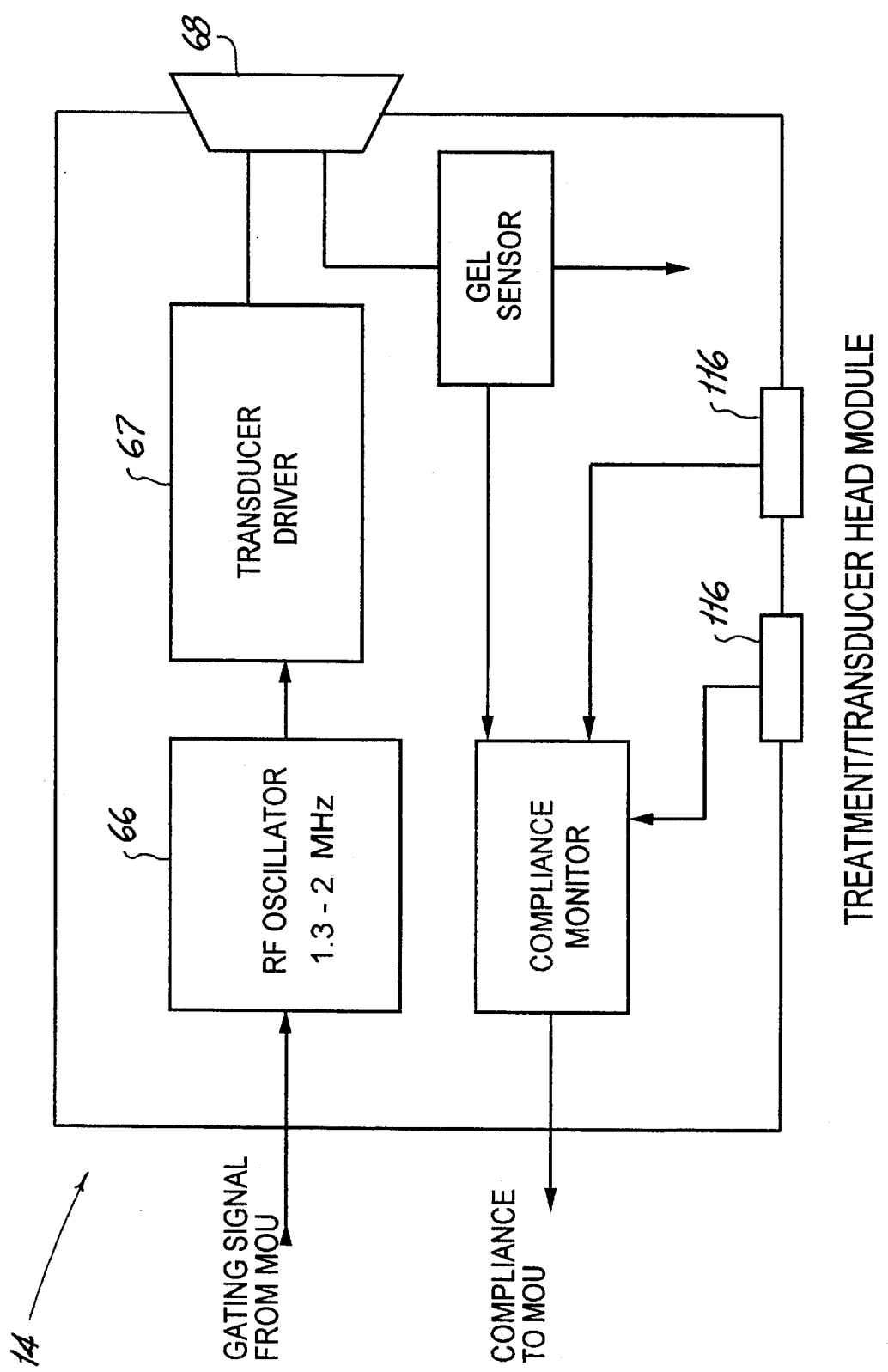
FIG. 6 is a block diagram of one embodiment of the circuitry for the ultrasonic transducer assembly.
Figure 6A:
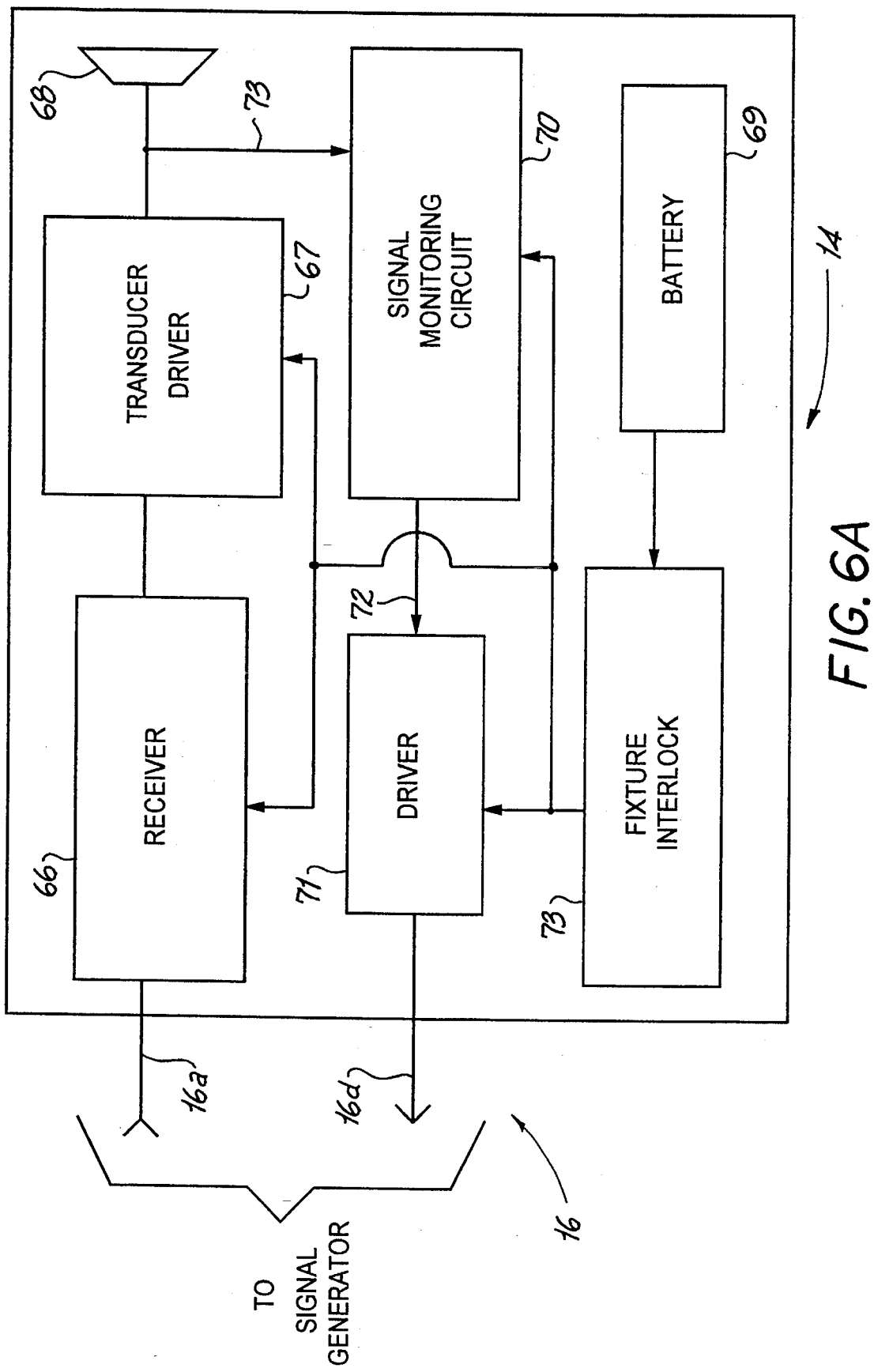
FIG. 6A is a block diagram of an alternative embodiment of the circuitry for the ultrasonic transducer assembly.

Referring to FIG. 6, a block diagram of one embodiment of the transducer treatment head module circuitry is shown. The transducer treatment head module circuitry includes a receiver 66 which receives the signals transferred by signal generator 12 via cable 16. Receiver 66 is connected to transducer driver 67 which excites transducer 68. An alternative embodiment of the transducer treatment head module circuitry is shown in FIG. 6A. In this embodiment, the transducer treatment head module 14 includes an internal battery 69 which supplies power to the internal components of the transducer treatment head module. For example, battery 69 supplies power to signal monitoring circuit 70 and signal driver 71. The signal monitoring circuit 70 provides, preferably, a digital output signal 72 which represents the waveform characteristics of the output of transducer driver 67. Such characteristics may include, for example, the frequency, pulse repetition frequency, the pulse width and the average output power of the signal driving transducer 68. The output signal 72 of signal monitoring circuit 70 is transferred to signal generator 12 via driver 71 and cable 16. Fixture interlock 73, which may include switches on the outer surface of the transducer treatment head module, provides power to the internal components of the transducer treatment head module 14 so as to ensure that the transducer treatment head module 14 is properly positioned before the transducer is excited. A more detailed description of this alternative embodiment is described in U.S. Pat. No. 5,003,965 which is incorporated herein by reference.

Although shown herein with a single transducer treatment head module, the present invention also envisions a plurality of modules for use with a single MOU.

Figure 7:
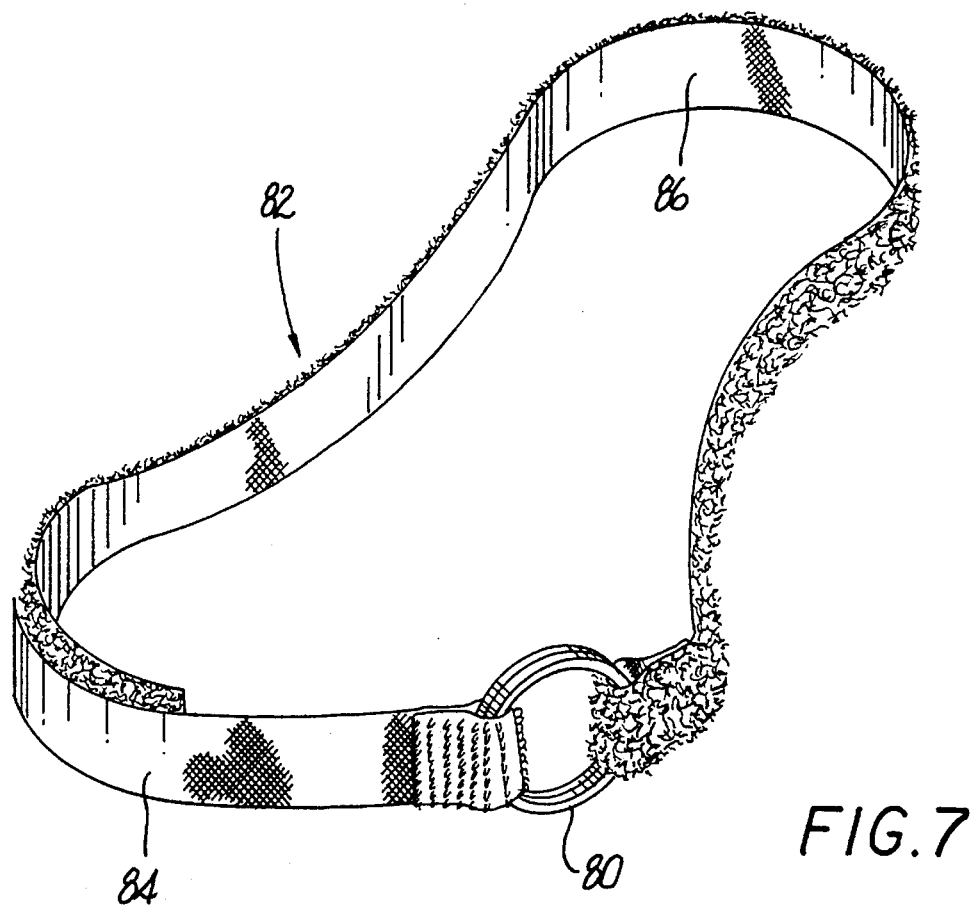
FIG. 7 is a perspective view of a locating ring and strap for locating bone injuries.
Figure 8:
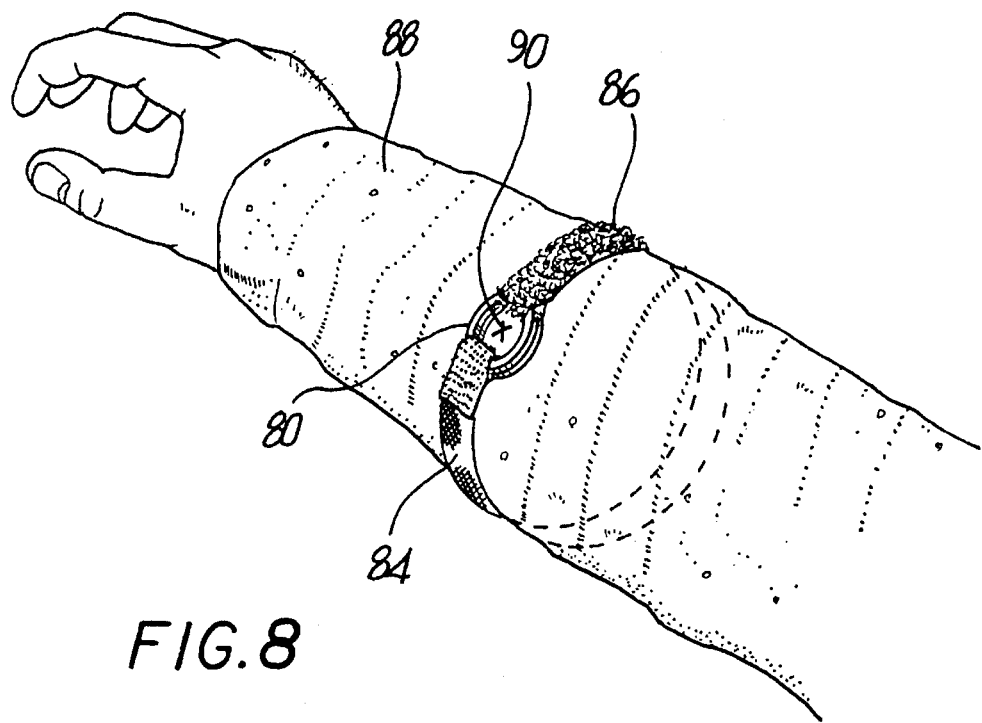
FIG. 8 is a perspective view of the locating ring of FIG. 7 affixed to a patient wearing a cast and illustrating a mark to define the location of a bone injury.

Referring now to FIG. 7, a locating ring 80 for determining the location of injured bone is shown. The locating ring 80 includes a strap 82 for releasably securing the ring to a patient. The strap 82 preferably has two sections 84 and 86 which permit quick fastening and unfastening of the ring 80 on and off the patient. The ring 80 is constructed of material that may be seen with a chosen medical visualizing system. Thus, if X-rays are used, the ring 80 is at least partially opaque to X-radiation. If infra-red radiation is used, the ring 80 is at least partially opaque to infra-red radiation, and, if magnetic resonance imaging is used, the ring 80 is at least partially paramagnetic. However, the other materials may be used for the ring which permits detection by medical visualizing or imaging systems.

The dimensions of the ring 80 are typically a function of the size of the patient, the estimated size and location of the injury, and the type of visualizing system used. For example, to determine the location of a bone fracture in an average human limb, e.g., the ulna or radius, and using an X-ray imaging system, the diameter of the ring may nominally be 1.5 inches. In this example, the ring may be a rigid torus of metallic material of cross-sectional diameter nominally 0.2 inches. As another example, if the visualization system utilized is an ultrasonic imaging system, the ring 80 may be substantially flexible and planar, so that it may contour to a surface it is placed adjacent to, thereby allowing the scanning or imaging transducer to be moved across the surface and the ring.

As noted, the strap 82 has two sections 84 and 86, each section has one end fastened to the ring 80. The two sections 84 and 86, preferably, have hook and loop type fastening assembly, such as VELCRO®, so that they may be fastened together and quickly unfastened. Other quick release fastening techniques are also contemplated.

FIGS. 8 through 12 illustrate locating an injured bone, affixing a fixture configured to maintain the transducer treatment head module adjacent the area of the injured bone, and connecting the ultrasonic transducer assembly to the fixture for treating the injured bone. Initially, the locator ring 80 is positioned on a cast 88 on, for example, a patient's arm, at a location corresponding to the estimated or approximated location of the injury. This initial position is a preliminary approximation of the external location of the bone injury, and may be based on previously taken X-rays, a physician's diagnosis or the patient's recall of the point of injury.

An external image, e.g., an X-ray, of the fractured region is taken to include the locating ring 80. Although the initial position of the locating ring 80 with respect to the bone injury is a preliminary approximation, in many instances the initial placement will be sufficiently accurate so that the X-ray will depict the bone injury framed by the ring 80. The resulting X-ray image indicates the position of the bone injury relative to the locating ring 80. The X-rays are used as a guide to locate and mark 90 the corresponding point on the cast relative to the actual locating ring 80. The mark 90 gives an approximate external location on the cast of the bone injury. If greater accuracy is required, the ring 80 may be centered about the mark 90, another X-ray is taken, and a new mark (not shown) is made on the cast based on the location of the bone fracture relative to the ring on the X-ray. Successive iterations of repositioning the locating ring 80 and X-raying the site will yield even greater accuracy.

Figure 9:
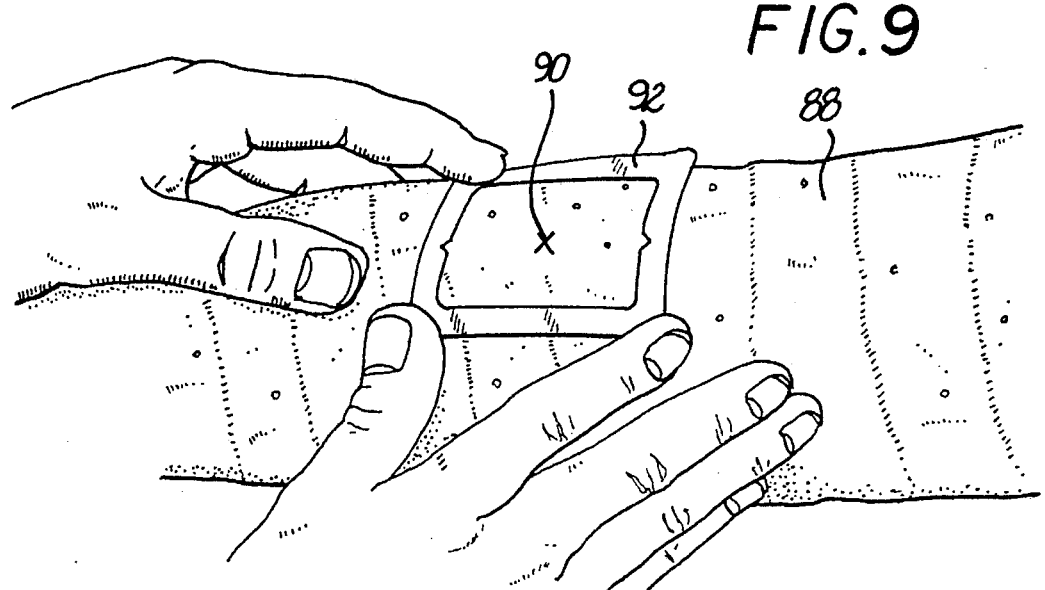
FIG. 9 is a perspective view of a template centrally located over the mark.
Figure 10:
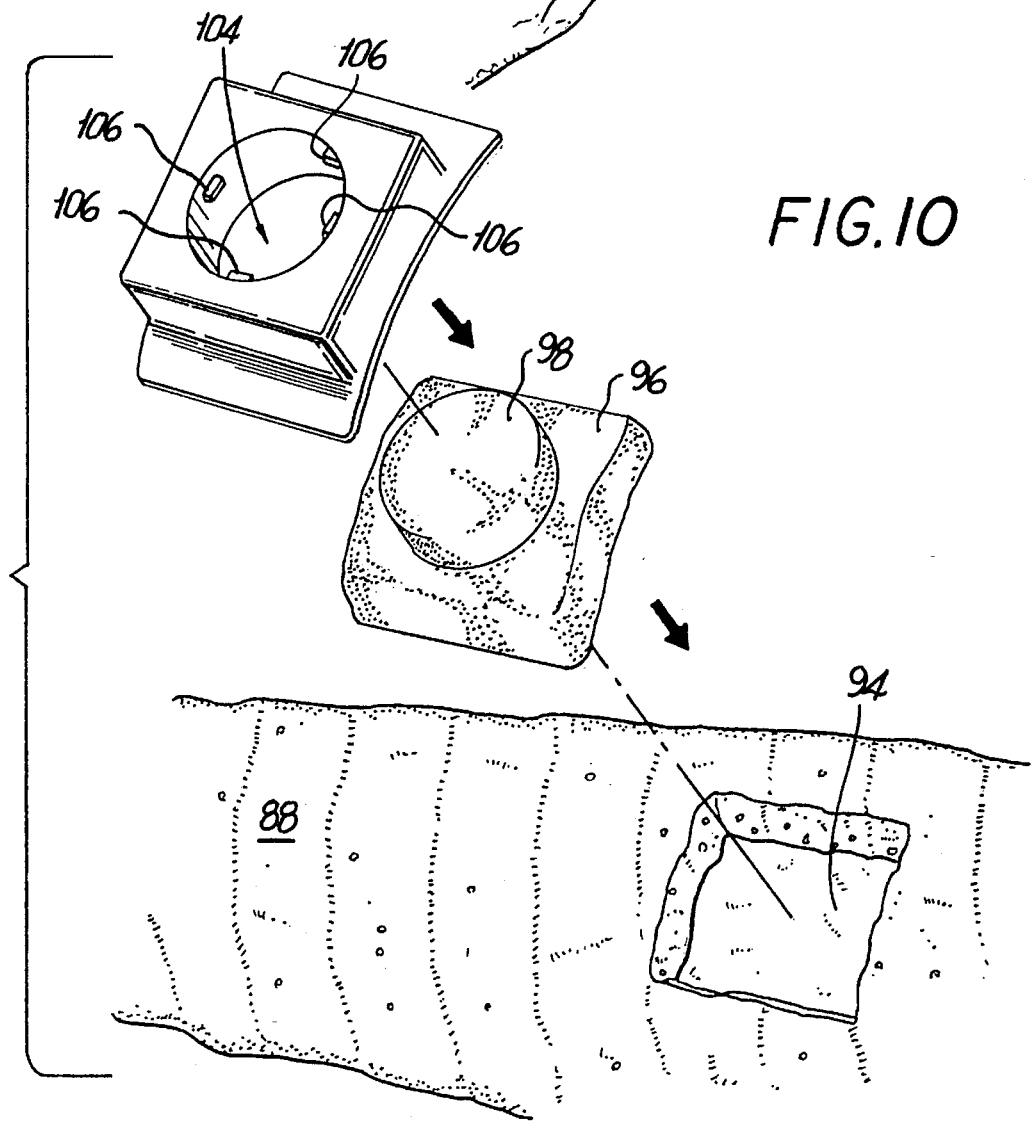
FIG. 10 is a perspective view with parts separated of the patient's cast with a removed section and a fixture for retaining and aligning the ultrasonic transducer assembly of FIG. 1.

As shown in FIGS. 9 and 10, a rectangular template 92 is pressed against the cast 88 and centered on the mark 90 of the external location on the cast 88 of the bone fracture. The outline of the inner edges of the template opening is traced on the cast 88, and the traced portion of the cast is removed so that the opening 94 in the cast 88 exposes the skin, as shown in FIG. 10. The opening 94 in the cast 88 receives a felt pad 96 having a thickness approximately the same as the thickness of the cast. The felt pad 96 also has a cylindrical bore that receives a cylindrical felt pad 98. Felt pad 96 is provided to support fixture 102 and to maintain pressure against the skin which helps prevent window edema (swelling) and is substantially equivalent to the pressure exerted by the cast 88 against the skin and is described in more detail below.

Preferably, the template 92, and consequently the opening 94 in the cast 88, is smaller than the flange 100 of a fixture 102 for retaining and aligning the ultrasonic transducer assembly 14, so that the flange 100 engages the cast surface surrounding the opening 94 when the fixture is placed over the opening 94. The fixture 102 also has a circular aperture 104 and bayonet locking lugs 106. Aperture 104 has substantially the same diameter as the cylindrical felt pad 98.

Figure 11:
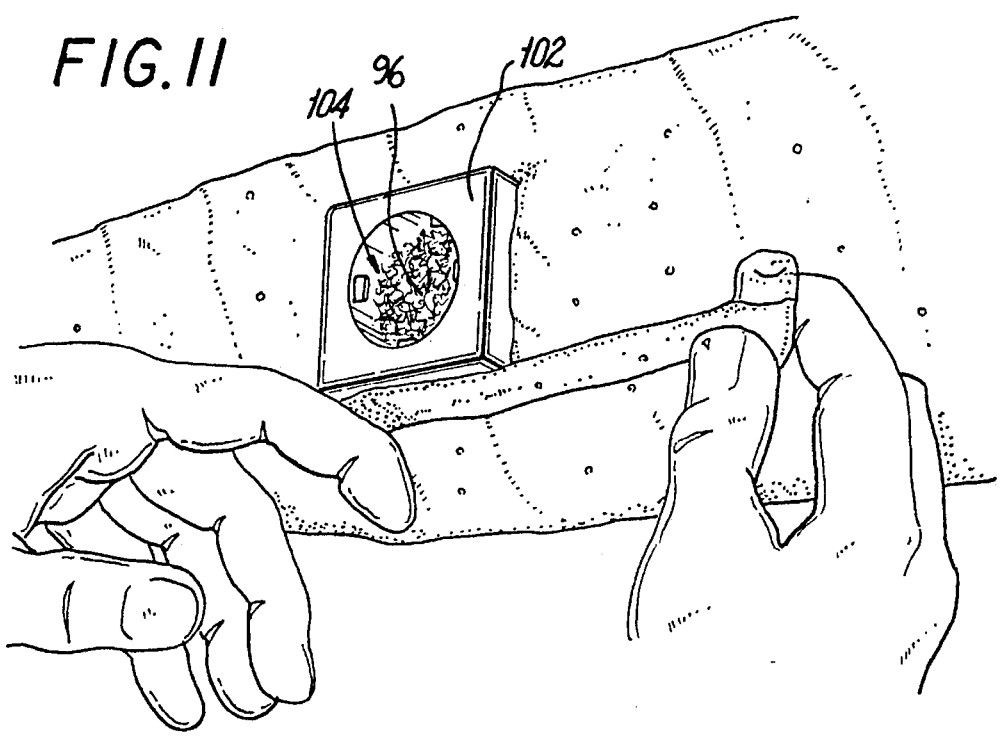
FIG. 11 is a perspective view of the fixture being secured to the cast at the removed section.

FIG. 11 shows the fixture 102 positioned over the opening 94 in the cast 88 and the felt pad 96 so that the aperture 104 and the cylindrical felt pad 98 are coaxially aligned. The fixture 102 partially compresses the felt pad 96, shown in FIG. 10, against the skin as flange 100 of fixture 102, shown in FIG. 8, engages the cast 88, thereby approximating the pressure of the removed portion of the cast where the felt pad engages the skin.

Figure 12:
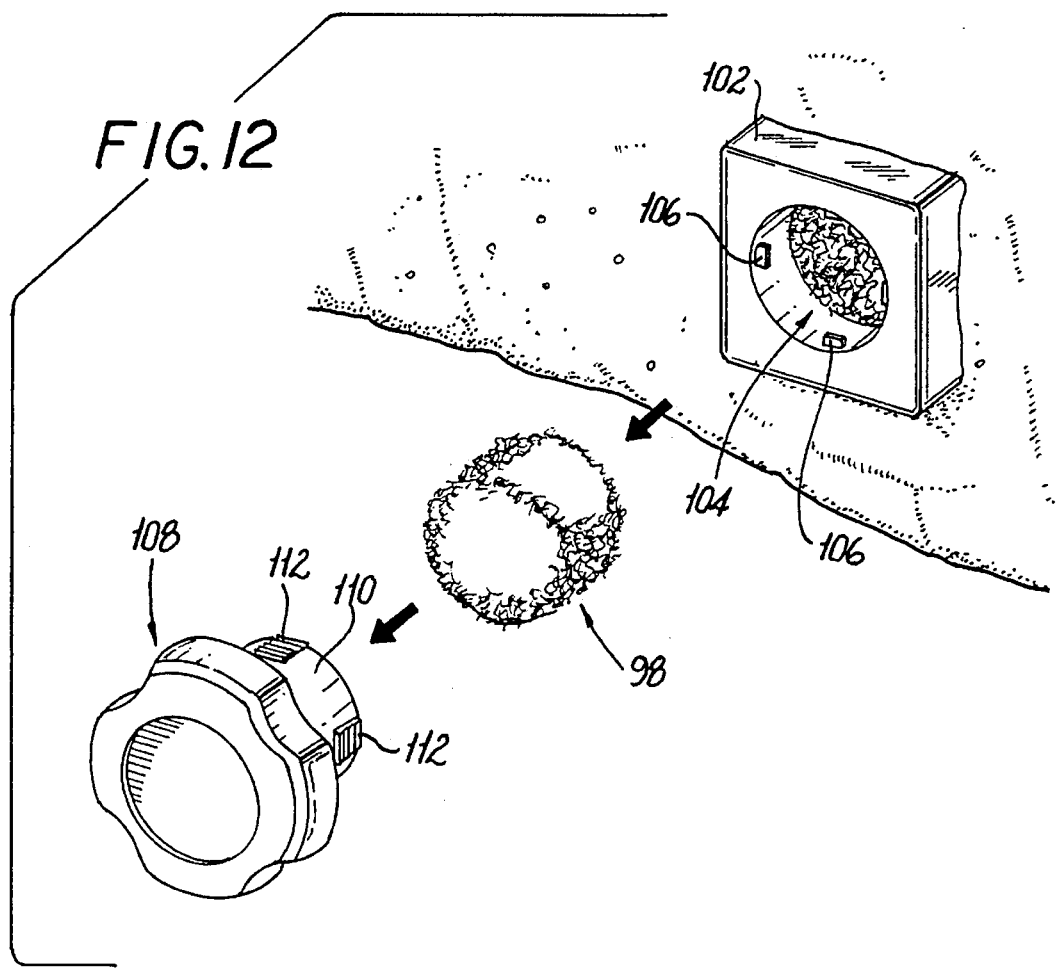
FIG. 12 is a perspective view with parts separated of the cast, the fixture and a cap for the fixture.

Referring to FIG. 12, a cap 108 for the fixture 102 is shown. The cap 108 is provided to maintain pressure on the body tissue exposed in fixture 102 when the ultrasonic treatment is completed. The cap 108 has a cylindrical portion 110 that extends into the aperture 104 of the fixture 102. The cap 108 has slotted lugs 112 on the cylindrical portion 110 that engage the bayonet lugs 106 in the fixture 102. The cylindrical felt pad 98 is positioned in the aperture 104 and the cylindrical portion 110 is inserted into the aperture 104 with the slotted lugs 112 offset from the bayonet lugs 106. The cap 108 is pressed against the cylindrical felt pad 98 until the pressure exerted by the cap 108 and cylindrical felt pad 98 against the skin approximates the pressure exerted by the cast 88 against the skin. (The cylindrical felt pad 98 may also be comprised of substantially planar circular layers that may be removed one layer at a time in order to adjust the thickness of the felt pad and the resulting pressure against the skin.) This pressure helps to inhibit window edemas. The cap 108 is then rotated so that its slotted lugs 112 engage the bayonet lugs 106.

Figure 13:
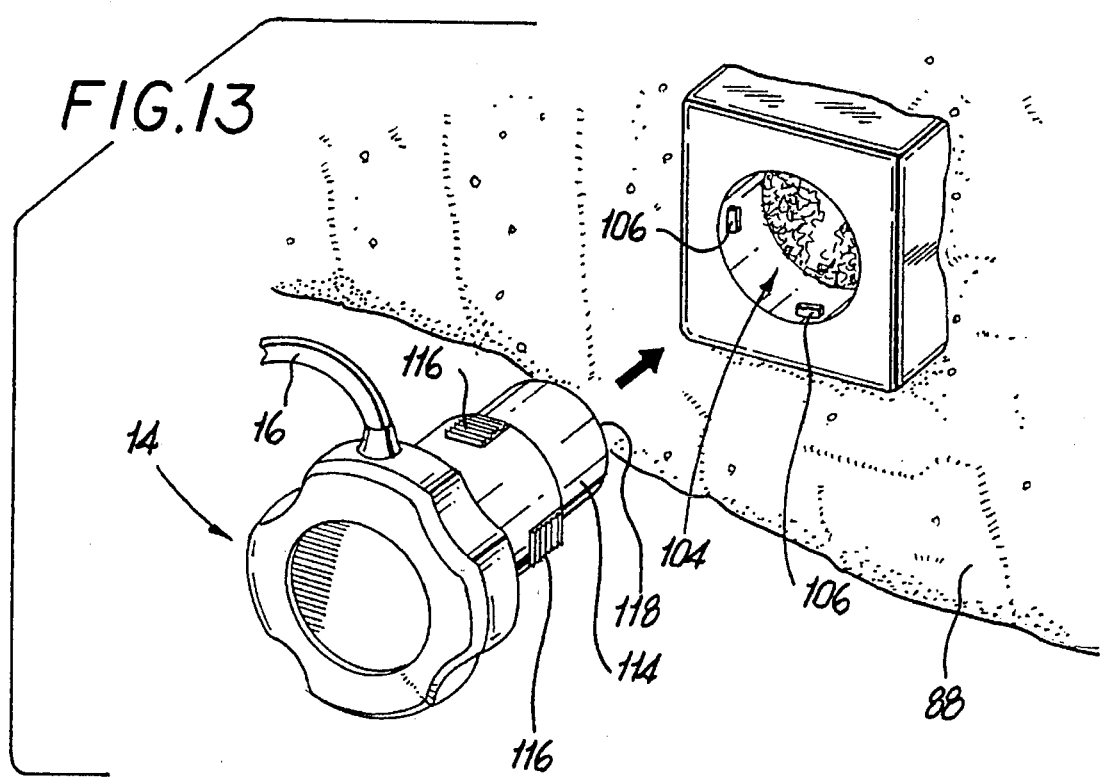
FIG. 13 is a perspective view with parts separated, illustrating the ultrasonic transducer assembly aligned for releasable attachment to the fixture.

FIG. 13 is a perspective view illustrating the alignment of the ultrasonic transducer treatment head module 14 with the fixture 102 for ultrasonic treatment of the injured bone. The transducer treatment head module projection 114 has slotted lugs 116 that engage the bayonet lugs 106 in the fixture 102. With the cap 108 and cylindrical felt pad 98, shown in FIG. 10, removed, the projection 114 fits into the aperture 104 of the fixture 102 and the bore of the felt pad 96, and is inserted with the slotted lugs 116 offset from the bayonet lugs 106. The operative surface 118 of the transducer treatment head module 14 is pressed adjacent the skin and the transducer treatment head module 14 is then rotated so that its slotted lugs 116 engage the bayonet lugs 106. The ultrasonic treatment then commences.

Referring again to FIGS. 5 and 6, to prevent inadvertent excitation of transducer treatment head module 14 and to insure compliance with treatment protocol, slotted lugs 116 are preferably fabricated from a conductive plastic and the bayonet lugs 106 in fixture 102 are electrically connected, such that when the slotted lugs 116 engage the bayonet lugs 106 an electrical path is completed between at least two of the slotted lugs 116. Suitable conductive plastics which may be utilized include conductive ABS plastics with either carbon, stainless steel, nickel or aluminum fibers.

Preferably, the operative surface 118 of transducer treatment head module 14 includes a gel sensing element for confirming the presence of ultrasonic conductive material on the operative surface 118. This surface 118 is pre-coated with a coupling gel before it is inserted in the fixture 102 and engages the skin. Alternatively, the gel may be contained adjacent the operative surface 118 of transducer treatment head module 14 using a gel sack, gel bladder or like container.

It will be understood that various modifications can be made to the various embodiments of the present invention herein disclosed without departing from its spirit and scope. For example, various shapes of the pouch and signal generator are contemplated, as well as various types of construction materials. Also, various modifications may be made in the configuration of the components used to excite the ultrasonic transducer. Therefore the above description should not be construed as limiting the invention but merely as presenting preferred embodiments of the invention. Those skilled in the art will envision other modifications within the scope and spirit of the present invention as defined by the claims presented below.

What is claimed is:

1. An apparatus for ultrasonically treating an injury comprising:

a portable self-contained main operating unit having an internal power source and dimensioned to be carried by a patient during treatment, a support fixture configured and adapted for attachment adjacent an external site corresponding to an internal injury remote from said main operating unit, and an ultrasonic transducer treatment head module operatively connected to said main operating unit and including means for detachably engaging said support fixture, said treatment head module having an ultrasonic signal generator and signal generator circuitry operatively associated therewith, said main operating unit having a display panel coupled to said signal generator circuitry to display treatment sequence data and a keypad coupled to said signal generator circuitry to permit user control, of said signal generator, said signal generator circuitry including a processor, means for generating a pulsed signal, and a switch coupled to said processor for regulating said pulsed signal.

2. The apparatus according to claim 1 further comprising a pouch, wherein said main operating unit is positioned within said pouch and worn by the patient to permit portable operation thereof.

3. The apparatus according to claim 1 further comprising an optical transmitter connected to said switch, said optical transmitter being configured to convert said pulsed signal to an optical signal.

4. The apparatus according to claim 1 further comprising a communication interface connected between a communication port and said processor to provide a communication link between said ultrasonic signal generator and an external computer/modem.

5. The apparatus according to claim 4, wherein said communication interface is a serial communication interface.

6. The apparatus according to claim 1 further comprising an alarm connected to said processor to indicate accurate compliance with a treatment protocol.

7. The apparatus according to claim 1, wherein said fixture has an aperture configured to receive a portion of said ultrasonic transducer treatment head module and at least two bayonet lugs extending into said aperture which are electrically connected to form a conductive path therebetween.

8. The apparatus according to claim 7, wherein said ultrasonic transducer treatment head module includes at least two slotted lugs having at least a portion thereof extending from an outer surface of said module and configured to engage said at least two bayonet lugs, said at least two slotted lugs being fabricated from conductive plastic such that when said slotted lugs engage said bayonet lugs a conductive path is formed between said slotted lugs.

9. A kit for ultrasonically treating injuries while maintaining patient mobility, which comprises:
- a support fixture configured and adapted to be worn by a patient adjacent an external site of an internal injury;
- an ultrasonic transducer treatment head module including an ultrasonic signal generator and means for detachably engaging said support fixture;
- a portable self-contained main operating unit operatively connected to said treatment head module and including means for facilitating user control of said signal generator; and
- a pouch dimensioned and configured to receive and maintain said main operating unit in a location remote from said support fixture, said pouch including a support belt adapted to be worn by a patient during treatment to afford mobility.

10. The kit according to claim 9, wherein said fixture includes an aperture configured to receive a portion of said ultrasonic transducer treatment head module and at least two bayonet lugs extending into said aperture, which are electrically connected to form a conductive path therebetween.

11. The kit according to claim 10, wherein said ultrasonic transducer treatment head module includes at least two slotted lugs having at least a portion thereof extending from an outer surface of said transducer treatment head module and configured to engage said at least two bayonet lugs, said at least two slotted lugs being fabricated from conductive plastic such that when said slotted lugs engage said bayonet lugs a conductive path is formed between said slotted lugs.

12. The kit according to claim 9, wherein said ultrasonic signal generator includes signal generator circuitry and an internal power source connected to said signal generator circuitry, a display coupled to said signal generator circuitry to display treatment sequence data, a keypad coupled to said signal generator circuitry to permit user control and/or entry of data, said signal generator circuitry including a processor, means for generating a pulsed RF signal, and a switch coupled to said processor for regulating said pulsed RF signal.

13. The kit according to claim 12 further comprising a communication interface connected between a communication port and said processor to provide a communication link between said ultrasonic signal generator and an external computer.

14. The kit according to claim 9 further comprising a cap, engagable with said fixture to replace said ultrasonic transducer treatment head module when the module is not being used for treatment.

15. The kit according to claim 14 further comprising a pad, configured and adapted to be positioned between said cap and a skin surface of said patient for applying a predetermined pressure to said skin surface.

16. The kit according to claim 9 further comprising a shoulder harness attached to said belt to provide additional support for the pouch.

* * * * *